US008017137B2

(12) United States Patent
Bartholomew

(10) Patent No.: US 8,017,137 B2
(45) Date of Patent: Sep. 13, 2011

(54) CUSTOMIZED RETAIL POINT OF SALE DISPENSING METHODS

(76) Inventor: Julie R. Bartholomew, Birmingham, MI (US)

(*) Notice: Subject to any disclaimer, the term of this patent is extended or adjusted under 35 U.S.C. 154(b) by 1419 days.

(21) Appl. No.: 11/183,668

(22) Filed: Jul. 18, 2005

(65) Prior Publication Data
US 2006/0024342 A1 Feb. 2, 2006

Related U.S. Application Data

(60) Provisional application No. 60/589,150, filed on Jul. 19, 2004.

(51) Int. Cl.
G06Q 10/00 (2006.01)
A61K 8/02 (2006.01)

(52) U.S. Cl. ............................................ 424/401; 705/2

(58) Field of Classification Search .................. None
See application file for complete search history.

(56) References Cited

U.S. PATENT DOCUMENTS

| | | |
|---|---|---|
| 967,938 A | 8/1920 | Krause |
| 1,912,899 A | 6/1933 | Johannsen |
| D90,897 S | 10/1933 | Rockola |
| D96,564 S | 8/1935 | Simpkins |
| 2,393,371 A | 1/1946 | Harris |
| 2,417,677 A | 3/1947 | Cohan |
| D192,180 S | 2/1962 | Hodgman |
| D192,301 S | 2/1962 | Schaef |
| 3,024,583 A | 3/1962 | Gastright |
| 3,471,611 A | 10/1969 | Scott et al. |
| 3,527,236 A | 9/1970 | Anthony et al. |
| 3,598,284 A | 8/1971 | Wessely |
| 3,688,947 A | 9/1972 | Reichenberger |
| 3,692,027 A | 9/1972 | Ellinwood, Jr. |
| 3,860,015 A | 1/1975 | Tarro |
| 4,003,379 A | 1/1977 | Ellinwood, Jr. |
| D248,693 S | 7/1978 | Housman |
| 4,133,525 A | 1/1979 | Balles et al. |
| 4,146,029 A | 3/1979 | Ellinwood, Jr. |
| 4,160,271 A | 7/1979 | Grayson et al. |
| 4,176,762 A | 12/1979 | Scalera et al. |
| 4,271,192 A | 6/1981 | Wurtman et al. |
| 4,281,664 A | 8/1981 | Duggan |
| 4,299,220 A | 11/1981 | Dorman |
| 4,351,591 A | 9/1982 | Stockett |
| 4,434,467 A | 2/1984 | Scott |
| 4,461,401 A | 7/1984 | Sasnett, Jr. |
| 4,470,987 A | 9/1984 | Wurtman et al. |
| 4,544,371 A | 10/1985 | Dormandy, Jr. et al. |
| 4,556,063 A | 12/1985 | Thompson et al. |
| 4,561,850 A | 12/1985 | Fabbri et al. |
| 4,628,974 A | 12/1986 | Meyer et al. |
| 4,651,716 A | 3/1987 | Forester et al. |
| 4,674,518 A | 6/1987 | Salo |
| 4,681,546 A | 7/1987 | Hart |
| 4,686,987 A | 8/1987 | Salo et al. |
| 4,705,083 A | 11/1987 | Rossetti |
| 4,764,044 A | 8/1988 | Konose |
| 4,830,218 A | 5/1989 | Shirkan |
| 4,838,457 A | 6/1989 | Swahl et al. |
| 4,846,184 A | 7/1989 | Comment et al. |
| 4,871,262 A | 10/1989 | Krauss et al. |
| 4,887,410 A | 12/1989 | Gandini |
| 4,897,987 A | 2/1990 | Spalla |
| D306,808 S | 3/1990 | Thomas |
| 4,909,632 A | 3/1990 | Simpson |
| 4,953,985 A | 9/1990 | Miller |
| 4,966,205 A | 10/1990 | Tanaka |
| 4,967,938 A | 11/1990 | Hellenberg |
| 4,987,897 A | 1/1991 | Funke |
| 5,014,698 A | 5/1991 | Cohen |
| 5,040,533 A | 8/1991 | Fearnot |
| 5,041,107 A | 8/1991 | Heil, Jr. |
| 5,042,497 A | 8/1991 | Shapland |
| 5,042,691 A | 8/1991 | Maldonado |
| 5,044,520 A | 9/1991 | Moisan |
| 5,058,581 A | 10/1991 | Silvian |
| D322,542 S | 12/1991 | Fontlladosa |
| 5,078,302 A | 1/1992 | Hellenberg |
| 5,083,591 A | 1/1992 | Edwards et al. |
| 5,111,855 A | 5/1992 | Boeck et al. |
| 5,116,134 A | 5/1992 | Edwards et al. |
| 5,119,973 A | 6/1992 | Miller et al. |
| D327,695 S | 7/1992 | Edstrom |
| D327,895 S | 7/1992 | Edstrom |
| 5,137,367 A | 8/1992 | Madonia et al. |
| 5,163,010 A | 11/1992 | Klein |
| 5,163,484 A | 11/1992 | Howlett et al. |
| 5,193,720 A | 3/1993 | Mayberry |
| 5,197,802 A | 3/1993 | Miller et al. |

(Continued)

FOREIGN PATENT DOCUMENTS

CA 98986 3/2003

(Continued)

OTHER PUBLICATIONS

US 6,568,560, 5/2003, Bartholomew et al. (withdrawn). www.vinovenue.net (Jan. 19, 2005), NPR Interview Transcript regarding same.
Steve Inskeep, National Public Radio hosts about VinoVenue (a wine tasting bar in San Francisco, http://www.vinovenue.net/), National Public Radio, copyright 2004.
Website at www.reflect.com, Jan. 25, 2002.
Website at www.threecustom.com, Jan. 25, 2002.
Website at www.colorlab-cosmetics.com, Jan. 25, 2002.
Pamphlet of Jovan, "Express your individuality," Feb. 17, 2000.
Website at www.immedia.it—"Coty Introduces Jovan Individuality" pp. 1-3 (accessed Jun. 8, 2001).
Website at www.cpcpkg.com, Feb. 17, 2003.
Website at www.fast-fluid.com—"TiNTiA (hair dye dispenser" p. 2 (accessed May 18, 2004).
Information from www.cosmetics.com/custblnd.htm, Oct. 11, 2000.
Evans, "An Introduction to Color", John Wiley & Sons, Inc, New York, 1948, pp. 87-90.
Wyszecki et al., "Color Science; Concepts and Methods, Quantitative Data and Formulae", 2nd Edition, A. Wiley Intescience Publication, p. 63, Aug. 8, 2000.

(Continued)

Primary Examiner — Shanon A Foley
(74) Attorney, Agent, or Firm — Dobrusin & Thennisch PC

(57) ABSTRACT

Methods for customizing products at a retail point of sale. A user interface is provided at the point of sale for selection of the desired product. Based upon the selection, ingredients are dispensed for making the personalized consumer product.

20 Claims, No Drawings

U.S. PATENT DOCUMENTS

| | | | |
|---|---|---|---|
| 5,203,387 A | 4/1993 | Howlett et al. | |
| 5,267,178 A | 11/1993 | Berner | |
| 5,267,669 A | 12/1993 | Dixon et al. | |
| 5,268,620 A | 12/1993 | Hellenberg | |
| 5,268,849 A | 12/1993 | Howlett et al. | |
| 5,271,527 A | 12/1993 | Haber et al. | |
| 5,271,628 A | 12/1993 | Okada | |
| 5,305,917 A | 4/1994 | Miller et al. | |
| 5,310,257 A | 5/1994 | Altieri, Jr. et al. | |
| 5,311,293 A | 5/1994 | MacFarlane et al. | |
| 5,312,240 A | 5/1994 | Divone, Sr. et al. | |
| 5,313,267 A | 5/1994 | MacFarlane et al. | |
| D347,645 S | 6/1994 | Miller | |
| D347,646 S | 6/1994 | Mayberry | |
| 5,328,057 A | 7/1994 | Hellenberg et al. | |
| D349,506 S | 8/1994 | Caruso et al. | |
| 5,356,041 A | 10/1994 | Hellenberg | |
| 5,361,812 A | 11/1994 | Arneson et al. | |
| 5,368,196 A | 11/1994 | Hellenberg et al. | |
| 5,379,916 A | 1/1995 | Martindale et al. | |
| 5,397,134 A | 3/1995 | Fishman et al. | |
| D357,142 S | 4/1995 | Jones et al. | |
| 5,407,100 A | 4/1995 | Tracy et al. | |
| 5,460,297 A | 10/1995 | Shannon et al. | |
| 5,478,238 A | 12/1995 | Gourtou et al. | |
| D366,304 S | 1/1996 | Lewis | |
| 5,480,288 A | 1/1996 | Hellenberg et al. | |
| 5,495,338 A | 2/1996 | Gouriou et al. | |
| 5,507,575 A | 4/1996 | Rossetti | |
| 5,524,656 A | 6/1996 | Konarski et al. | |
| 5,531,710 A | 7/1996 | Dang et al. | |
| 5,537,211 A | 7/1996 | Dial | |
| 5,549,372 A | 8/1996 | Lewis | |
| D374,677 S | 10/1996 | Hodson et al. | |
| 5,562,109 A | 10/1996 | Tobiason | |
| 5,562,643 A | 10/1996 | Johnson | |
| 5,566,693 A | 10/1996 | Gunderman et al. | |
| 5,612,868 A | 3/1997 | Off et al. | |
| 5,622,692 A | 4/1997 | Rigg et al. | |
| 5,626,155 A | 5/1997 | Saute | |
| 5,626,260 A | 5/1997 | Waldner | |
| 5,632,314 A | 5/1997 | Koppe et al. | |
| 5,636,637 A | 6/1997 | Guiolet et al. | |
| 5,643,341 A | 7/1997 | Hirsch et al. | |
| 5,647,411 A | 7/1997 | Koppe et al. | |
| 5,668,633 A | 9/1997 | Cheetam et al. | |
| 5,687,322 A | 11/1997 | Deaton et al. | |
| 5,690,252 A | 11/1997 | Oleksiewicz et al. | |
| 5,692,291 A | 12/1997 | Deevi et al. | |
| 5,697,527 A | 12/1997 | Altieri, Jr. et al. | |
| 5,711,458 A | 1/1998 | Langeveld et al. | |
| 5,711,601 A | 1/1998 | Thomas et al. | |
| 5,715,314 A | 2/1998 | Payne et al. | |
| 5,716,150 A | 2/1998 | Gueret | |
| 5,717,750 A | 2/1998 | Adams, Jr. et al. | |
| 5,720,017 A | 2/1998 | Cheetam et al. | |
| 5,724,424 A | 3/1998 | Gifford | |
| 5,730,330 A | 3/1998 | Reading | |
| D393,150 S | 4/1998 | Swanston et al. | |
| 5,771,524 A | 6/1998 | Woods et al. | |
| 5,778,901 A | 7/1998 | Abrahamian | |
| 5,785,510 A | 7/1998 | Altieri, Jr. et al. | |
| 5,785,960 A | 7/1998 | Rigg et al. | |
| 5,797,750 A | 8/1998 | Gouriou et al. | |
| 5,813,420 A | 9/1998 | Sussman | |
| D401,246 S | 11/1998 | Langeveld et al. | |
| 5,841,421 A | 11/1998 | Cheetam et al. | |
| 5,842,641 A | 12/1998 | Mazzalveri | |
| 5,860,809 A | 1/1999 | Meehan | |
| 5,862,947 A | 1/1999 | Wiegner et al. | |
| 5,867,403 A | 2/1999 | Sasnett et al. | |
| 5,897,204 A | 4/1999 | Dittmer et al. | |
| 5,903,465 A | 5/1999 | Brown | |
| 5,904,421 A | 5/1999 | Mazzalveri | |
| 5,906,433 A | 5/1999 | Mazzalveri | |
| 5,924,426 A | 7/1999 | Galazin | |
| 5,931,166 A | 8/1999 | Weber et al. | |
| 5,938,080 A | 8/1999 | Haaser et al. | |
| 5,944,227 A | 8/1999 | Schroeder et al. | |
| 5,945,112 A | 8/1999 | Flynn et al. | |
| 5,960,411 A | 9/1999 | Hartman et al. | |
| 5,971,351 A | 10/1999 | Swaab | |
| 5,972,322 A | 10/1999 | Rath et al. | |
| 5,982,501 A | 11/1999 | Benz et al. | |
| 5,984,146 A | 11/1999 | Kaufman | |
| 5,992,691 A | 11/1999 | Post et al. | |
| 5,993,792 A | 11/1999 | Rath et al. | |
| 6,000,407 A | 12/1999 | Galazin | |
| 6,002,488 A | 12/1999 | Berg et al. | |
| 6,003,731 A | 12/1999 | Post et al. | |
| 6,021,362 A | 2/2000 | Maggard et al. | |
| 6,035,860 A | 3/2000 | Mombourquette | |
| 6,035,867 A | 3/2000 | Barrick | |
| 6,056,158 A | 5/2000 | Rossetti et al. | |
| 6,065,969 A | 5/2000 | Rifkin et al. | |
| 6,073,834 A | 6/2000 | Michael et al. | |
| 6,089,538 A | 7/2000 | Shirkhan | |
| 6,119,895 A | 9/2000 | Fugere et al. | |
| 6,139,429 A | 10/2000 | Shoemaker, Jr. | |
| 6,158,997 A | 12/2000 | Post | |
| 6,177,093 B1 * | 1/2001 | Lombardi et al. | 424/401 |
| D437,151 S | 2/2001 | Gerstmar | |
| 6,182,555 B1 | 2/2001 | Scheer et al. | |
| 6,186,686 B1 | 2/2001 | Neuner et al. | |
| 6,198,536 B1 | 3/2001 | Baker | |
| 6,200,210 B1 | 3/2001 | Pratt | |
| 6,202,895 B1 | 3/2001 | Fox | |
| D442,405 S | 5/2001 | Gerstmar | |
| 6,264,786 B1 | 7/2001 | Cromett | |
| 6,270,273 B1 | 8/2001 | Ohba | |
| 6,273,298 B1 | 8/2001 | Post | |
| 6,293,284 B1 | 9/2001 | Rigg | |
| 6,297,420 B1 | 10/2001 | Heincke | |
| 6,318,596 B1 | 11/2001 | Wiesner | |
| 6,338,030 B1 | 1/2002 | Senn et al. | |
| 6,338,349 B1 | 1/2002 | Robinson et al. | |
| 6,371,129 B1 | 4/2002 | Le Bras-Brown et al. | |
| 6,382,269 B1 | 5/2002 | Tatsuno | |
| 6,383,542 B1 | 5/2002 | Khodor et al. | |
| 6,402,120 B1 | 6/2002 | Swaab | |
| 6,412,658 B1 | 7/2002 | Bartholomew et al. | |
| D461,080 S | 8/2002 | Bartholomew et al. | |
| D465,810 S | 11/2002 | Bartholomew et al. | |
| 6,510,366 B1 | 1/2003 | Murray et al. | |
| 6,516,245 B1 | 2/2003 | Dirksing et al. | |
| 6,557,369 B1 | 5/2003 | Phelps et al. | |
| 6,588,085 B2 * | 7/2003 | Holloway | 29/527.4 |
| 6,607,100 B2 | 8/2003 | Phelps et al. | |
| 6,615,881 B2 | 9/2003 | Bartholomew et al. | |
| 6,622,064 B2 | 9/2003 | Bartholomew et al. | |
| 6,663,818 B2 | 12/2003 | Statham et al. | |
| D485,310 S | 1/2004 | Bartholomew et al. | |
| 6,672,341 B2 * | 1/2004 | Bartholomew et al. | 141/18 |
| 6,779,686 B2 | 8/2004 | Bartholomew et al. | |
| 6,782,307 B2 | 8/2004 | Wilmott et al. | |
| D500,804 S | 1/2005 | Bartholomew et al. | |
| 6,883,561 B2 | 4/2005 | Bartholomew | |
| D513,040 S | 12/2005 | Bartholomew | |
| 7,082,970 B2 | 8/2006 | Bartholomew et al. | |
| 7,099,740 B2 | 8/2006 | Bartholomew et al. | |
| 7,121,429 B2 | 10/2006 | Bartholomew et al. | |
| 7,134,573 B2 | 11/2006 | Post | |
| 7,174,310 B2 | 2/2007 | Bartholomew et al. | |
| 2001/0000802 A1 | 5/2001 | Soykan et al. | |
| 2001/0044579 A1 | 11/2001 | Pratt | |
| 2002/0010528 A1 | 1/2002 | Bartholomew et al. | |
| 2002/0084288 A1 | 7/2002 | Lewis et al. | |
| 2002/0109270 A1 | 8/2002 | Swaab | |
| 2002/0131985 A1 | 9/2002 | Shana'a et al. | |
| 2002/0136744 A1 | 9/2002 | Margosiak et al. | |
| 2003/0014324 A1 * | 1/2003 | Donovan et al. | 705/26 |
| 2003/0060854 A1 | 3/2003 | Zhu | |
| 2003/0062379 A1 * | 4/2003 | Bartholomew et al. | 222/1 |
| 2003/0098314 A1 | 5/2003 | Phelps et al. | |
| 2003/0151611 A1 | 8/2003 | Turpin et al. | |
| 2004/0002739 A1 | 1/2004 | Cates et al. | |
| 2004/0004309 A1 | 1/2004 | Sears | |

| | | | |
|---|---|---|---|
| 2004/0122553 A1 | 6/2004 | Phan et al. | |
| 2004/0243361 A1 | 12/2004 | Steuben et al. | |
| 2006/0004311 A1 | 1/2006 | Hargrave et al. | |
| 2006/0124196 A1 | 6/2006 | Bartholomew et al. | |
| 2006/0283521 A1 | 12/2006 | Bartholomew et al. | |
| 2007/0194038 A1 | 8/2007 | Bartholomew et al. | |
| 2008/0047972 A1 | 2/2008 | Bartholomew et al. | |

FOREIGN PATENT DOCUMENTS

| | | |
|---|---|---|
| DE | 4110299 C1 | 2/1993 |
| DE | 40202765.5 | 3/2002 |
| EP | 0443741 B1 | 8/1991 |
| EP | 0446512 B1 | 1/1995 |
| EP | 0682236 B1 | 11/1995 |
| EP | 0686997 A2 | 12/1995 |
| EP | 0871022 | 10/1998 |
| EP | 1093842 | 4/2001 |
| EP | 3002418 | 2/2003 |
| EP | 1429640 | 3/2007 |
| EP | 2000089 | 12/2008 |
| FR | 021986 | 3/2002 |
| GB | 3002418 | 3/2002 |
| GR | 3062096 | 6/2007 |
| JP | 04-231006 | 8/1992 |
| JP | 05-025020 | 2/1993 |
| JP | 05-107115 | 4/1993 |
| JP | 05-233651 | 9/1993 |
| JP | 07-243908 | 9/1995 |
| JP | 07-270396 | 10/1995 |
| JP | 08-050125 | 2/1996 |
| JP | 08-280633 | 10/1996 |
| JP | 09-10033 | 1/1997 |
| JP | 09-038045 | 2/1997 |
| JP | 09-133584 | 5/1997 |
| JP | 09-178560 | 7/1997 |
| JP | 10-339670 | 12/1998 |
| JP | 11-169231 | 6/1999 |
| JP | 11-218447 | 8/1999 |
| JP | 11-265443 | 9/1999 |
| JP | 2001-126140 | 2/2001 |
| JP | 11-66435 | 1/2003 |
| SU | 1704759 | 1/1992 |
| WO | 95/05892 | 3/1995 |
| WO | 98/05417 | 2/1998 |
| WO | 98/30189 | 7/1998 |
| WO | 99/34905 | 7/1999 |
| WO | 99/61234 | 12/1999 |
| WO | 00/64570 | 11/2000 |
| WO | 01/12239 | 2/2001 |
| WO | 01/91601 | 6/2001 |
| WO | 01/75586 | 10/2001 |
| WO | 01/91600 | 12/2001 |
| WO | 02/05200 | 1/2002 |
| WO | 03/026458 | 4/2003 |
| WO | 2006/020189 | 2/2006 |
| WO | 2006/052863 | 5/2006 |

OTHER PUBLICATIONS

Cheskin, L. "Color Guide for Marketing Media", The MacMillan Co., 1954, pp. 133-140.
Lovett, P.A., et al., "Measurement of the Skin Colour of Babies in Hospital," National Lighting Conference 1986, pp. 140-154.
"The Shades of You; Your Color Palette," "Your New Image Through Color & Line", California Fashion Image, Crown Summit Books, 1981, pp.
Shibatani, J., et al., "Measurements of Aging Effects of Facial Color Distribution and Applications," J. Soc. Cosmet. Chem. Japan, vol. 19 No. 1, 1985, pp. 48-52.
Website at www.idexcorp.com/groups/fluidmgt.asp—"Fluid Management" pp. 1-2 (accessed May 18, 2004).
Supplementary European Search Report dated Apr. 6, 2004 (1026.001EP).
Search Report dated May 23, 2003 (1026-017WO).
Partial International Search PCT/US2005/025384 dated Nov. 16, 2005(1026-021WO).
International Search Report for PCT/US2005/025384 dated Mar. 29, 2006 (1026-021WO).
International Search PCT/US2005/040240 dated Apr. 3, 2006 (1026-022WO).
EP Office Action for Serial No. 01 922 731.3-2307, Applicant IMX Labs, Inc. dated Jun. 17, 2005.
EP Office Action for Serial No. 02 763 648.9-2313, Applicant IMX Labs, Inc. dated Jun. 6, 2005.
Extended EP Search Report for EP2000089A1 dated Nov. 11, 2008 (1026.001EP2).

* cited by examiner

CUSTOMIZED RETAIL POINT OF SALE DISPENSING METHODS

CLAIM OF BENEFIT OF FILING DATE

The present application claims the benefit of the filing date of U.S. Provisional Application Ser. No. 60/589,150 (Filed Jul. 19, 2004), the entirety of the contents of this provisional application being hereby expressly incorporated by reference.

TECHNICAL FIELD

The present invention relates to devices and methods for the customized personalized consumer products at a retail point of sale.

BACKGROUND OF THE INVENTION

The present invention is an improvement to subject matter of previous commonly-owned applications and patents including U.S. Pat. Nos. 6,412,658; 6,622,064; 6,672,341; 6,615,881; D465,810; D461,080; and D485,310 and Ser. No. 10/755,574 (filed Jan. 12, 2004), Ser. No. 10/437,085 (filed May 13, 2003), Ser. No. 10/848,273 (filed May 18, 2004), Ser. No. 10/274,514 (filed Oct. 18, 2002), Ser. No. 10/716,317 (filed Nov. 18, 2003); Ser. No. 29/192,696 (filed Oct. 28, 2003), the contents of which are also incorporated by reference herein for all purposes.

As addressed in the above applications and patent, historically the cosmetics industry has afforded consumers a broad variety of choices for colors (including tones, shades or hues) and effects. In the typical scenario, these products are pre-packaged according to a predetermined fixed amount of different colors or effects. The products are then ordinarily displayed to reveal a spectrum of a fixed number of colors. However, because of manufacturing and other practical limitations, point of sale displays only afford a finite number of selections for the consumer. Consequently, the consumer's choice of color will be limited by present availability or supply of a particular color choice, and also particularly by the specific colors chosen for sale in advance by the manufacturer. The consumer is afforded no practical opportunity to custom blend a color selection.

In view of the foregoing, a need has developed for a custom cosmetic color selection system, pursuant to which a consumer or other customer (such as an intermediate retailer or wholesaler) can interact with the supplier to select a specific color, effect or both, to blend the resulting cosmetic product at or near the time of selection (e.g. on site at a point of sale location, or remotely such as by mail order, phone order or internet purchase).

Furthermore, there is a need for a custom cosmetic color selection system that allows for the customization of cosmetic products to dispensed for a variety of different applications. Such products include: moisturizing strips, dental bleaching, hair removal, spot removal, stretch mark fading strip, expression line/wrinkle minimizer, lip plumper patch, acne treatment, scar minimizer, hair bleaching, cellulite reducer, artistic/photograph/text image transfers in edible or non-edible formulations, cosmeceutical sticks, eye crayons, lip pencils, cheek stain sticks, lipsticks, concealer sticks, foundation sticks, perfume sticks, sunscreen stick, deodorant stick, aromatherapy candles, hair removal sticks, shimmer sticks, scrub sticks, antibacterial towelette, moisturizing towelette, dental bleaching towelette, hair removal towelette, bronzer towelette, body shimmer towelette, hair shimmer/color towelette, makeup remover towelette, nail polish remover, acne treatment towelette, hair bleaching towelette, deodorant towelette, perfume towelette, sun protection towelette, exfoliation towelette or anti-aging towelette, eye shadows, lip shimmer, face shimmer powder, face powder foundation, body powder shimmer, brow powder, face blushers, bronzers, eye liners, body paint, facial soap bars, body soap bars, sliced soap, pliable soap, a brush, an applicator, sponge, puff, patch, lash curler, comb, tweezers, clippers may be customized by size, design, material, or coloration.

SUMMARY OF THE INVENTION

Methods for customizing products at a retail point of sale. A user interface is provided at the point of sale for selection of the desired product. Based upon the selection, ingredients are dispensed for making the personalized consumer product.

DESCRIPTION OF THE INVENTION

In one aspect, the present invention meets the above needs and contemplates providing a customized retail point of sale cosmetic patch dispenser. The custom cosmetic is dispensed onto a substrate using techniques such as spraying, printing, rolling dipping, combinations thereof or the like. Any cosmetic ingredient, pigment, glitter product, powder, oil or water based solution to be applied to a plastic, paper, fabric, or metal substrate for eventual transfer of the cosmetic to the skin, hair, nail, fabric (i.e.; inside of an eye patch for cosmetic delivery), or teeth (whitening products) to the consumer.

The substrate may have an adhesive backing and/or a protective film layer for easy application. Ingredients may be transferred through the epidermal/dermal barrier via electrical impulse from a printed battery that is attached to the patch or a carrier that is present in the composition of the cosmetic product. A computer will be present at Retail Point of Sale to allow the customer or technician to direct the process of preparing the specific result that would further customize the end product to the customer's specification at the point of sale. A Radio Frequency Identification Device (RFID), retinal scan, smart card, thumb print recognition software may identify and collect preparation information for the client.

The substrate may be precut or stamped or may be cut at point of sale for specific placement of the patch. The ingredient may be sprayed, printed, drawn, rolled on by a roller, heat applied or dipped into a solution for cosmetic application. Process: Substrate layer will be put into position for active ingredient application. Active ingredients and/or image/design is applied via nozzle, syringe, image printer/inkjet, dipping procedure or other physical transfer to substrate layer and may be set by heating, freezing, air, or chemical curing process.

Products derivable from this aspect of the present invention includes: moisturizing strips, dental bleaching, hair removal, spot removal, stretch mark fading strip, expression line/wrinkle minimizer, lip plumper patch, acne treatment, scar minimizer, hair bleaching, cellulite reducer, artistic/photograph/text image transfers in edible or non-edible formulations.

In another aspect, the present invention provides a customized retail point of sale heated liquid (e.g., hot pour) to cooled solid cosmetic dispenser. The cosmetic ingredients may be selected from any cosmetic ingredient, pigment, glitter product, powder, oil or water based solution is stored as a solid or liquid within the dispenser. The cosmetic ingredients may be heated and combined at point of retail sale for the delivery into a mold, pot, glass container, pencil casing, plastic applicator or other package utilized by the final customer. After the liquid is transferred into its application package it may be cooled, vacuum packed, microwaved, etched, coated or otherwise treated to complete the formulation process that would further customize the end product to the customer's specification at the point of sale.

Preferably, a computer is present at Retail Point of Sale to allow the customer or technician to direct the process of preparing the specific result. An RFID, retinal scan, smart card, thumb print recognition software may identify and collect preparation information for the client.

Products derivable from this aspect of the present invention includes: cosmeceutical sticks, eye crayons, lip pencils, cheek stain sticks, lipsticks, concealer sticks, foundation sticks, perfume sticks, sunscreen stick, deodorant stick, aromatherapy candles, hair removal sticks, shimmer sticks, scrub sticks.

In another aspect, the present invention provides a customized retail point of sale Cosmetic Towelette Infusion Dispenser. The cosmetic ingredients may be selected from any cosmetic ingredient, pigment, glitter product, powder, oil or water based solution to be applied/infused to a plastic, sponge, paper, fabric, or metal substrate to be packaged or sealed into a paper, plastic, fabric, glass, or metal container/pouch for delivery of the final product. It should be appreciated that a towelette may be defined as any of the previously mentioned materials that exists in a thin form that is to be used expressly for storage and eventual delivery of a formulation to the skin, hair, nail, or clothing by a wiping, compression, or blotting motion.

The present invention provides a computer at Retail Point of Sale to allow the customer or technician to direct the process of preparing the specific result that would further customize the end product to the customer's specification. A radio frequency identification device (RFID), retinal scan, smart card, thumb print recognition software may identify and collect preparation information for the client.

The formulation ingredients may be sprayed, printed, drawn, rolled on, heat applied or towelette may be dipped into a solution for formulation application.

In one embodiment the process includes the following steps: placing a substrate layer (towelette) into position for active ingredient application; an active ingredients and/or image/design is applied via nozzle, syringe, image printer/inkjet, dipping procedure or other physical transfer process to towelette; the treated towelette may be set by heating, cooling, air, chemical or other curing process; the treated towelette is then packaged appropriately to maintain product integrity and to facilitate final use by customer.

Products derivable from this aspect of the present invention includes: antibacterial towelette, moisturizing towelette, dental Bleaching towelette, hair removal towelette, bronzer towelette, body shimmer towelette, hair shimmer/color towelette, makeup remover towelette, nail polish remover, acne treatment towelette, hair bleaching towelette, deodorant towelette, perfume towelette, sun protection towelette, exfoliation towelette or anti-aging towelette.

In another aspect, the present invention provides a customized retail Point of sale cosmetic pressed powder dispenser. The custom cosmetic pressed powder dispensing method, including the steps of providing a powder mixture dispensing apparatus combined with pressing apparatus to form a powder "cake." The "cake" shall be defined as a solidified representation of a loose powder mixture that has had several pounds of pressure applied to the mixture while resting in a tray from which it is dispensed into at retail point of sale with customer specifications through a computer interface and a physical selection process. The amounts and types of the powder mixture ingredients dispensed are also determined based upon specification by a retail customer. Any powder based cosmetic formulation may include pigment, glitter product, oil or water based solution, which are stored within the dispenser.

In one embodiment the method includes the steps of: A loose cosmetic powder (for face and/or body) dispensed through a cartridge, tube, syringe, slide, or straw; a puff of air, electronic vibration, ratchet-type or pumping movement will allow the powder to be properly metered and delivered to a container; several to hundreds of pounds of pressure are applied via a cylindrical weight that will make contact with the loose powder mixture that has been delivered to a tin or plastic tray beneath the dispense point of the powder. After the cylindrical weight is retracted from the powder mixture, the result is a cohesive, pressed form. This pressed form may then be etched, embossed, coated or otherwise altered to complete the formulation according to customer specification. This finished "cake" is subsequently packaged appropriately to maintain product integrity and to facilitate final usage by the customer (i.e.; a cosmetic compact). The cake may also be transferred into a fabric-enclosed puff for application.

Preferably, a computer will be present at Retail Point of Sale to allow the customer or technician to direct the process of preparing the specific result that would further customize the end product to the customer's specification. An RFID, retinal scan, smart card, thumb print recognition software may identify and collect preparation information for the client.

Products derivable from this aspect of the present invention includes eye shadows, lip shimmer, face shimmer powder, face powder foundation, body powder shimmer, brow powder, face blushers, bronzers, eye liners, body paint.

In another aspect, the present invention provides a customized retail Point of sale molded soap dispenser. The cosmetic soap dispenser that combines an array of ingredients that may be water based, glycerin based, oil based or a combination thereof including pigments, fragrance, glitter, powder, liquid powder, encapsulated oils, encapsulated granules composed of sand, food product (i.e.; oatmeal) or gelatinous material may be combined at retail point of sale for customer selection. Any of the above ingredients may be combined in any assortment via a computer interface that is available for the customer or technician at point of sale. In addition to ingredients, the customer may select a particular mold, shape, stamp or etched design that would further customize the end product to the customer's specification at the point of sale.

In one embodiment, the method includes the steps of: providing soap shavings that are either shredded in the machine or are stored inside the unit will be collected at a central point to be pressed and molded into a desired shape and size, the molded soap may be cut, pressed, squeezed, stamped, printed or embossed per direction of the customer; the unit will house and store letters, shapes, or pictures to be applied to or stamped into the finished soap product.

Preferably, a computer will be present at Retail Point of Sale to allow the customer or technician to direct the process of preparing the specific result that would further customize the end product to the customer's specification. An radio frequency identification device (RFID), retinal scan, smart card, thumb print recognition software may identify and collect preparation information for the client.

Products derivable from this aspect of the present invention includes: facial soap bars, body soap bars, sliced soap, pliable soap or the like.

In another aspect, the present invention provides a customized cosmetic tool, applicator and brush dispenser at retail point of sale. At the retail point of sale, a brush, an applicator, sponge, puff, patch, lash curler, comb, tweezers, clippers may be customized by size, design, material, or coloration for a customer via a computer interface located at the retail point of sale and allows the customer or technician to direct the process of preparing the specific result. A radio frequency identification device (RFID), retinal scan, smart card, thumb print recognition software may identify and collect preparation information for the client.

A machine capable of brush manufacture will house varying brush components and subsequently form brushes exactly matching customer specifications such as bristle type (i.e.; pony hair, sable, synthetic, hypoallergenic, colored), brush shape (i.e.; flat, round, angled, short bristled), brush or handle size, handle color/material, monogramming or other printed or etched design. Applicator, sponge, puff or patch dispenser will bring together at point of sale the appropriate components and subsequently form applicator, sponge, puff or patch to previously detailed customer specifications. These specifications could require various procedures such as infusion with a pigment, glitter product, powder, oil or water based solution applied via nozzle, syringe, image printer/inkjet, dipping procedure or other physical transfer to substrate layer and may be set by heating, freezing, air, or chemical curing process.

Unless stated otherwise, plural structural components step can be provided by a single integrated structure or step. Alternatively, a single integrated structure step might be divided into separate plural components or steps. However, it is also possible that the functions are integrated into a single component or step.

Any reference herein to "first" and "second" is not intended as limiting to combinations that consist of only first and second items. Where so-referenced, it is possible that the subject matter of the present invention may suitably incorporate third, fourth or more items. Moreover, the disclosure of "a" or "one" element or step is not intended to foreclose additional elements or steps.

In addition, while a feature of the present invention may have been described in the context of only one of the illustrated embodiments, such feature may be combined with one or more other features of other embodiments, for any given application. It will also be appreciated from the above that the fabrication of any unique structure herein and the operation thereof also constitutes processes in accordance with the present invention.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. A method of forming a retail point of sale customized cosmetic product, comprising:
   a. providing a computer operated user interface for the selection of a cosmetic product;
   b. providing a retail point of sale dispenser in communication with the computer operated user interface, the dispenser being adapted to dispense one or more cosmetic ingredients selected from pigment, glitter product, powder, oil or water based solution, or combinations thereof;
   c. selecting a customized cosmetic product using the computer operated user interface;
   d. dispensing at the retail point of sale one or more liquid cosmetic ingredients via the cosmetic dispenser into a receptacle selected from a mold, pot, glass container, pencil casing, or plastic applicator, wherein the receptacle is the package utilized by a final customer;
   e. treating the liquid cosmetic ingredients at the retail point of sale after dispensing the ingredients into a receptacle by a step of cooling, vacuum packaging, microwaving, etching, coating, or combinations thereof to form a customized cosmetic product selected from cosmetic sticks, eye crayons, lip pencils, cheek stain sticks, lipsticks, concealer sticks, foundation sticks, perfume sticks, sunscreen stick, deodorant stick, aromatherapy candles, hair removal sticks, shimmer sticks, or scrub sticks;
   f. heating the one or more cosmetic ingredients at the retail point of sale prior to dispensing; and
   g. etching or stamping the dispensed and treated ingredients at the point of sale.

2. The methods of claim 1, wherein the computer operated user interface is adapted to be used with a radio frequency identification device.

3. The method of claim 2, wherein the ingredients are dispensed into a mold by hot pouring.

4. The method of claim 2, wherein the package includes a custom brush.

5. The method of claim 4, wherein the ingredients are dispensed into a mold by hot pouring.

6. The method of claim 5, wherein the product is cooled.

7. The method of claim 4, further including the step of manufacturing the custom brush to match customer specifications.

8. The method of claim 7, further including the step of monogramming, printing, or etching a design on the brush.

9. The method of claim 7, wherein the brush components are varied from brush to brush so that components match customer specifications such as bristle type, brush shape, or brush size.

10. The method of claim 1, wherein the ingredients are dispensed into a mold by hot pouring.

11. The method of claim 10, wherein the product is cooled to a solid.

12. The method of claim 1, wherein the product is cooled to a solid.

13. The method of claim 12, wherein the ingredients are dispensed into a mold by hot pouring.

14. The method of claim 1, further including the step of forming a lip pencil by dispensing the ingredients into a pencil casing.

15. The method of claim 14, wherein the ingredients are dispensed into the pencil casing by hot pouring.

16. A method of forming a retail point of sale customized cosmetic product, comprising:
   a. providing a computer operated user interface for the selection of a cosmetic product;
   b. providing a retail point of sale dispenser in communication with the computer operated user interface, the dispenser being adapted to dispense one or more cosmetic ingredients selected from pigment, glitter product, powder, oil or water based solution, or combinations thereof;
c. selecting a customized cosmetic product using the computer operated user interface;
d. heating the one or more cosmetic ingredients at the retail point of sale prior to dispensing;
e. dispensing at the retail point of sale the heated one or more liquid cosmetic ingredients via the cosmetic dispenser into a receptacle selected from a mold, pot, glass container, pencil casing, or plastic applicator, wherein the receptacle is a package utilized by a customer;
f. treating the liquid cosmetic ingredients at the retail point of sale by a step of cooling, vacuum packaging, microwaving, etching, coating or combinations thereof to form a customized cosmetic product selected from cosmetic sticks, eye crayons, lip pencils, cheek stain sticks, lipsticks, concealer sticks, foundation sticks, perfume sticks, sunscreen stick, deodorant stick, aromatherapy candles, hair removal sticks, shimmer sticks, or scrub sticks;
h. cooling the heated cosmetic ingredients so that they form a solid in the receptacle;
i. etching or stamping the solidified cosmetic ingredients at the point of sale with a custom design selected by the customer; and
j. attaching a custom brush to the package;
wherein the computer operated user interface is adapted to be used with a radio frequency identification device, retinal scanner, smart card, or thumb print recognition system.

17. The method of claim 16, wherein the receptacle is a mold.

18. The method of claim 17, wherein the ingredients are microwaved after the ingredients are dispensed into the package.

19. The method of claim 16, wherein the receptacle is a glass container.

20. The method of claim 16, further including the steps of manufacturing a custom brush to match customer specifications;
monogramming, printing, or etching a design on the brush, and including the custom brush on the package.

* * * * *

UNITED STATES PATENT AND TRADEMARK OFFICE
CERTIFICATE OF CORRECTION

| | | |
|---|---|---|
| PATENT NO. | : 8,017,137 B2 | Page 1 of 1 |
| APPLICATION NO. | : 11/183668 | |
| DATED | : September 13, 2011 | |
| INVENTOR(S) | : Julie R. Bartholomew | |

It is certified that error appears in the above-identified patent and that said Letters Patent is hereby corrected as shown below:

Title Page 1, item (56) Other Publications: Column 2, "www.vinovenue.net (Jan. 19, 2005), NPR Interview Transcript regarding same." should start on a separate line.

Claim 16, Columns 7 and 8, lines 21-4: the paragraph letters h.; i.; and j. are incorrect and should read g., h., i.

Signed and Sealed this

Thirteenth Day of December, 2011

David J. Kappos
*Director of the United States Patent and Trademark Office*